United States Patent
Stadler et al.

(10) Patent No.: US 10,369,561 B2
(45) Date of Patent: Aug. 6, 2019

(54) SYRINGE HOUSING FOR PIPETTING A BIOLOGICAL MATERIAL, COMPRISING INTEGRATED MEMBRANES

(71) Applicant: Cell.Copedia GmbH, Leipzig (DE)

(72) Inventors: Herbert Stadler, Niemetal (DE); Wilhelm Gerdes, Leipzig (DE); Sabine Przibilla, Leipzig (DE)

(73) Assignee: Cell.Copedia GmbH (DE)

( * ) Notice: Subject to any disclaimer, the term of this patent is extended or adjusted under 35 U.S.C. 154(b) by 240 days.

(21) Appl. No.: 15/535,044

(22) PCT Filed: Dec. 10, 2015

(86) PCT No.: PCT/EP2015/079279
§ 371 (c)(1),
(2) Date: Jun. 10, 2017

(87) PCT Pub. No.: WO2016/092025
PCT Pub. Date: Jun. 16, 2016

(65) Prior Publication Data
US 2017/0361314 A1    Dec. 21, 2017

(30) Foreign Application Priority Data
Dec. 10, 2014 (DE) .................. 20 2014 105 965 U

(51) Int. Cl.
*G01N 1/00* (2006.01)
*B01L 3/02* (2006.01)
(Continued)

(52) U.S. Cl.
CPC .............. *B01L 3/0217* (2013.01); *B01L 9/54* (2013.01); *G01N 35/1011* (2013.01);
(Continued)

(58) Field of Classification Search
CPC ....................................................... G01N 1/00
See application file for complete search history.

(56) References Cited

U.S. PATENT DOCUMENTS

| 3,902,849 A | 9/1975 | Barak et al. |
| 5,336,412 A | 8/1994 | Huse et al. |

FOREIGN PATENT DOCUMENTS

| DE | 102008050750 A1 | 4/2010 |
| EP | 0476997 A2 | 3/1992 |

OTHER PUBLICATIONS

"Cell.Copedia", Aug. 29, 2014, pp. 1-2, XP055253276, Retrieved from the Internet: URL: http://www.cellcopedia.com/news.html.

*Primary Examiner* — Jyoti Nagpaul
(74) *Attorney, Agent, or Firm* — Riverside Law LLP

(57) ABSTRACT

A first aspect of the invention relates to a syringe housing which can have the following elements: a syringe body which has a first open end and a second open end, a first channel being formed between the two ends; a first membrane which is arranged such that the membrane extends substantially perpendicularly to the longitudinal direction of the first channel over the cross-section thereof; a syringe body attachment which has a first open end and a second open end, a second channel being formed between the two ends; a second membrane which is arranged such that the membrane extends substantially perpendicularly to the longitudinal direction of the second channel over the cross-section thereof; wherein the second open end of the syringe body and the first open end of the syringe body attachment are designed so as to be connectable in a formfitting manner and thus form the syringe housing, the first channel and the second channel form a continuous channel in the connected state of the syringe housing, and the first membrane and the second membrane define an extraction volume in the region of the continuous channel. Furthermore, different embodi- (Continued)

ments provide a pipette device which is designed for the automatic use of the syringe housing according to the invention.

20 Claims, 6 Drawing Sheets

(51) Int. Cl.
 B01L 9/00 (2006.01)
 G01N 35/10 (2006.01)
 B01L 3/00 (2006.01)
(52) U.S. Cl.
 CPC ........... B01L 3/502 (2013.01); B01L 2200/02 (2013.01); B01L 2200/023 (2013.01); B01L 2300/0609 (2013.01); B01L 2300/0681 (2013.01); B01L 2300/0848 (2013.01); G01N 2035/1025 (2013.01)

SYRINGE HOUSING FOR PIPETTING A BIOLOGICAL MATERIAL, COMPRISING INTEGRATED MEMBRANES

Syringes are nowadays widely used and are indispensable, inter alia, in the medical sector as well as biotechnology. Syringes can be used like a cartridge or column, for example, for the purification of biological materials such as cells, viral particles or liposomes by affinity chromatography. Such methods for purification of biological materials by affinity chromatography are described, for example, in International Patent Application WO 2013/124474 and the publications cited therein. For such purification processes the syringes can be divided into two parts. To this end, two membranes are provided near the inlet/outlet opening, which define a region between them in which a functionalized matrix material can be present which serves for the selective separation of biological materials such as proteins, cells or other biological moieties such as liposomes or virus particles. The functionalized matrix material can be, for example, polymer beads (beads) such as agarose beads or glass beads. The surface of the matrix material (for example, an agarose or a glass bead) is usually coated with a special binding reagent. The binding reagent can be, for example, an antibody molecule that specifically binds to a surface molecule of the biological material, for example an antibody or an antibody fragment against a surface receptor located on the surface of a particular cell population (see, WO 2013/124474). Upon introducing a liquid sample containing a certain biological material to be isolated into the syringe, the biological material (e.g. cells of the immune system such as T cells) binds to the matrix material with which the syringe is filled and on which, for example, suitable antibody molecules are immobilized, and can be selectively purified/isolated from the liquid by means of affinity chromatography. A syringe configured for the purification of a biological material can also be referred to as an affinity chromatography column.

Such generally cylindrical syringes, which are produced entirely from plastic, must ensure, on the one hand, maximum, in the optimum case, absolute tightness between the rubber plug of the plunger and the inner surface of the cylinder for the suction and pressure stroke of a piston supported displaceably therein. On the other hand, a slow fluid transport which requires minimal physical effort is desirable.

In known syringes, the tips thereof are usually designed to be thin, so that the piston can be moved for transporting fluids to or from the syringe interior only with a certain force. In addition, depending on the speed at which the piston is moved in the syringe interior, the injection syringe with a thin design causes a turbulent liquid flow, which in biochemical cell purification procedures may be undesirable. Usually, known syringes are also designed to be quite thin, so that their holding volumes are too small for many applications.

It is an object of the invention to provide a device which solves the above-described problems, i.e., for example, a syringe which can ensure a liquid flow free of turbulence in the interior as well as upon entering/exiting, as well as enabling a displacement of the piston with minimal physical effort.

This object is achieved by the present invention, in particular, the object is achieved by the following aspects of the present invention, such as devices, methods or uses and embodiments thereof, as well as by the subject matter of the claims. The figures illustrate the present invention. There is also provided a device in which agarose can be easily filled and "locked".

In a first aspect, the invention relates to a syringe housing for pipetting a biological material, wherein the syringe housing can have the following elements:

a syringe body which has a first open end and a second open end, a first channel being formed between the two ends;

a first membrane which is arranged such that the membrane extends substantially perpendicularly to the longitudinal direction of the first channel over the cross-section thereof;

a syringe body attachment which has a first open end and a second open end, a second channel being formed between the two ends;

a second membrane which is arranged such that the membrane extends substantially perpendicularly to the longitudinal direction of the second channel over the cross-section thereof;

wherein the second open end of the syringe body and the first open end of the syringe body attachment are designed so as to be connectable in a formfitting manner and thus form the syringe housing.

The first channel and the second channel form a continuous channel in the connected state of the syringe housing, and the first membrane and the second membrane define an extraction volume in the region of the continuous channel. In the following, the syringe housing according to the invention for pipetting a biological material can be abbreviated as syringe housing.

Within the scope of this description, a syringe housing can be understood to mean a generally, but not necessarily, cylindrical column having an opening at each of its ends and into which usually various liquid substances, such as sample solutions (e.g. full blood, serum or plasma), buffer solutions, or biological materials such as, e.g., cells in aqueous phase can be introduced or have already been introduced. In the presence of membranes in the interior of the syringe housing between which a matrix material is arranged or in other words when the syringe housing has an extraction region filled with a matrix material, a syringe configured in this way can serve as a column for chromatographic purification for various biotechnological and/or chemical processes such as, e.g., protein or cell purification of material from various sources. In this context, in the various embodiments of the syringe housing any biological material can be used that can be subjected to a chromatographic purification such as, e.g., affinity chromatography, but also, for example, gel permeation chromatography (also referred to as size exclusion chromatography). Examples of biological materials are all the materials described in international patent application WO 2013/124474, such as cells, viral particles, liposomes, or organelles such as mitochondria or chloroplasts. Examples of cells include prokaryotic and eukaryotic cells. Examples of prokaryotic cells are bacterial cells such as *E. coli* or *Bacillus subtilis*, examples of eukaryotic cells are yeast cells, insect cells and mammalian cells including human cells. Mammalian cells can be, e.g., cells of the immune system such as lymphocytes (e.g. T cells, B cells, natural killer cells), stem cells or certain body cells such as pancreatic or liver cells. All these cells carry specific surface molecules by means of which the cells can be isolated from a sample by affinity chromatography purification. In a preferred embodiment, the syringe housing according to the invention serves as a "selection cartridge" as described in international patent application WO 2013/124474 (cf., Example 1). A preferred application of this embodiment of the syringe housing and the associated pipette device of the present invention is the purification of cells of the immune system, such as, e.g., B cells or T cells on a preparative scale. The syringe housing and the pipette device of the present invention thus allows, e.g., a simple, fast and economical purification of body cells for medical or biochemical research purposes.

For forming a syringe, the syringe housing according to the invention can be equipped with a corresponding piston, which can be moved manually or automatically within the syringe. In the following, a syringe according to the invention is understood to mean a syringe housing according to the invention, into which a piston is inserted. At the back end of the syringe housing, i.e., at the end where the plunger can be inserted into the syringe, a finger flange may be attached. The finger flange can be used to fix or lock the syringe housing. In cooperation with a thumb part of a piston inserted into the syringe housing, the finger flange can facilitate the displacement of a piston inserted into the syringe housing—automated by means of a corresponding device, or manually.

The membranes can be frits the pore size of which can be configured to the particular application. The membranes can have such a pore size such that the liquid media and buffer solutions used in an application as well as the biological material to be purified can pass unimpeded, but the membranes can retain the matrix material located between them securely and reliably. In other words, the pore size of the membranes may be chosen to be smaller than the smallest diameter or the smallest dimension of the particles of the matrix material, but greater than the largest dimension of the particles or molecules in the aqueous phases used. Typically, the pore size can be any value in the range of a few micrometers, i.e., about 1 µm, 2 µm, or 3 µm up to a few hundred micrometers, for example, 100 µm, 200 µm, 500 µm.

Both the first membrane and the second membrane extend over the entire cross-section of the channel formed in the interior of the syringe housing and are arranged substantially perpendicular to its longitudinal direction, this channel being formed by the first channel and the second channel in the connected state of the syringe housing. In other words, the first channel can transition continuously into the second channel. The matrix material may be present in the subsection of the channel between the two membranes, hereinafter referred to as the extraction region or extraction volume. By specifically positioning the first membrane within the first channel and the second membrane within the second channel, on the one hand the volume of extraction region can be set freely, and on the other hand its relative position within the channel can also be set.

In the assembled state of the syringe housing, the syringe body and the syringe body attachment form a form-fitting unit, and the first channel is aligned with the second channel without changing the channel diameter at the transition. In other words, in the assembled state of the syringe housing, the first channel transitions continuously into the second channel. Optionally, a gasket may be provided between the syringe body and the syringe body attachment, but it is not required, since an externally sealed syringe housing is formed by the form-fitting connection of the syringe body and the syringe body attachment. According to various embodiments, the components of the syringe housing, i.e., the syringe body, the syringe body attachment and the two membranes can be formed from suitable plastics. However, the components, for example can also be made of glass or metallic materials if this should be regarded as advantageous for a particular application, for example, when highly corrosive media are used.

The first membrane and the second membrane define the extraction volume in the region of the continuous channel. Prior to assembling the syringe housing the extraction volume can be filled with a matrix material. The two membranes can be selected with regard to their pore size such that the liquid can flow through the extraction volume, but the matrix material cannot pass through the membranes. In this context, a pore size of 50 µm may be mentioned as an example, which is sufficiently large to allow, for example, all the substances present during cell purification to pass through, but to retain the matrix material, which can be present, for example, in the form of beads which can have a diameter in the range of 50 µm, effectively in the extraction volume. The extraction volume can be configured to the particular application and ultimately depends both on the diameter of the channel and on the distance between the two membranes. In the case of syringe housings with a channel diameter of about 5 mm, the extraction volume can have a volume of about 200 µl, and in those with a channel diameter of about 1 cm, the extraction volume can have a volume of 1 ml to about 2 ml. It should be stressed that the above figures are for the sole purpose of illustrating the possible scale and should not be regarded as technical limitations.

In further embodiments of the device according to the invention, the first membrane can be formed integrally with the inner wall of the syringe body. For example, the first membrane can be secured in a firmly bonded manner to the inner wall of the syringe body or firmly bonded by means of its edge in the inner wall of the syringe body by being introduced into the syringe body already during the injection molding process of the syringe body. As a result, the first membrane can be integrally formed with the syringe body. From this aspect, it may be added that no additional holding elements, such as retainers or support rings, are required to fix the first membrane in the syringe body at a desired position in the first channel. Such holding elements can generally interfere with the fluid mechanics within the first channel or the channel formed by the syringe body since they can narrow the channel abruptly and/or in a step-like manner and, in addition, particles can become entangled in the contact region between such holding elements and the inner wall of the channel. Both are effects that are undesirable in laboratory analysis. In the syringe housing described herein, such effects can be avoided by the direct anchoring/securing of the first membrane in or on the inner wall of the first channel. Instead during injection molding, the first membrane can be introduced into the syringe body by separating said syringe body at the desired location along a plane perpendicular to its longitudinal expansion, placing the first membrane between the two separated parts, and then bringing together these two syringe body parts. The two syringe body parts can be assembled, for example, thermally or by using a suitable adhesive. From the viewpoint of a liquid flowing through the first channel or the channel, the first membrane represents a singular disruption in the otherwise continuously smooth inner wall of the first channel or the channel, the axial extent of this singular disruption being in the order of magnitude of the thickness of the first membrane and can thus be in the range of about 30 µm to about 150 µm, whereby depending on the application and material of the membrane, its thickness can also be larger or smaller. The statements made in this paragraph can apply in a manner with regard to securing the second membrane to or in the inner wall of the syringe body attachment.

In further embodiments of the device according to the invention, the diameter of the first channel in the region above the first membrane can essentially correspond to the diameter of the first channel in the region below the first membrane. This characteristic can be attributed to the integral attachment of the first membrane to or in the inner wall of the first channel, for which no additional holding means are required. Overall, the first channel can have a uniformly constant diameter, that is to say not tapered. The statements made in this paragraph can be transferred analogously to the diameter of the second channel in the region above and below the second membrane. The diameters of the first channel and the second channel can be, depending on requirements, between a few millimeters up to one centimeter and beyond. In practice, the diameter may ultimately be subject to standardization. For example, the diameter of the channel (and thus the first channel and the second channel) can be in the range of about 3 mm to about 5 mm for small syringe bodies. For large syringe bodies the diameter of the channel can be about 1 cm. The wall of the syringe body can be made of a plastic and have a thickness in the range of about 0.3 mm to about 3 mm.

In further embodiments of the device according to the invention, the transition within the first channel from a region above the first membrane to a region below the first membrane can be continuous. In this case, the relative expressions "above" and "below" are not to be regarded as limiting, but rather should be read as "behind" and "in front" or "left" and "right" (or vice versa) depending on the position of the syringe housing. The statements made in this paragraph may equally apply to the transition within the second channel with respect to the second membrane.

In further embodiments of the device according to the invention, the first membrane can be secured to the end of the first channel. In this context, the first membrane may be glued or otherwise secured to one side at the lower edge of the syringe body. When assembling the syringe housing, pressure can then be exerted on the other, non-adhered side of the first membrane by an area of the edge of the syringe body attachment formed correspondingly for the form-fitting connection. In other words, additional support can be provided to the first membrane by being clamped between the syringe body and the syringe body attachment.

In further embodiments of the device according to the invention, the second membrane can be secured to the second open end of the syringe body.

In further embodiments of the device according to the invention, the extraction volume can have a substantially uniform diameter, the diameter of which can substantially correspond to the diameter of the continuous channel.

In further embodiments of the device according to the invention, the second open end of the syringe body and the first open end of the syringe body attachment can designed in such a way that they form a one-way fastening. In other words, the corresponding ends of the syringe body and of the syringe body attachment, which are designed to form a form-fitting unit (i.e, the syringe housing) can, in the assembled state, form a non-detachable fastening. In the context of this application, a one-way fastening or a non-detachable fastening is understood to mean a fastening or a combination of components in which the components can not be detached from one another without a permanent destruction of the fastening structure. When using such a one-way fastening the syringe body and the syringe body attachment can not be detached and reassembled again. In this sense, a one-way fastening can be understood as a single-use fastening.

In further embodiments of the device according to the invention, the one-way fastening can have locking structures which are configured to prevent detachment of the syringe body from the syringe body attachment in the assembled state of the syringe housing. The one-way fastening can be implemented by means of fastening structures or locking structures which engage when assembling the syringe housing, for example, snap, and then are no longer detachable from one another, that is, without accepting a destruction of components. For example, in the case of the form-fitting assembly of the ends of the syringe body and the syringe body attachment at least one jagged structure can slide into an opening which is geometrically configured therewith, and is not detachable from this position.

In further embodiments of the device according to the invention, the one-way fastening can be a plug-in fastening or a rotary fastening. Furthermore, the one-way fastening can also have a mixed shape, that is to say a plug-in fastening combined with a rotary fastening. A plug-in fastening can be understood to mean a fastening in which the connector partners are predominantly plugged, pushed, or placed on top of one another. A rotary fastening can be understood to mean a fastening in which the connector partners are rotated predominantly against one another. However, the one-way fastening can also be a mixed form of the plug-in and rotary fastening.

In further embodiments of the device according to the invention, the second open end of the syringe body and the first open end of the syringe body can be designed wherein one of the open ends has an axially protruding collar which, in the assembled state of the syringe housing, engages with an inwardly stepped region of the corresponding other open end.

In further embodiments of the device according to the invention, the device may further have a piston which is supported axially displaceably in the interior of the syringe housing. By means of the piston, a vacuum or an overpressure can be generated in the channel within the syringe housing, as a result of which aqueous media can be displaced from the channel or aspirated into the channel.

In further embodiments, the device according to the invention can have a piston stop which is configured to limit the insertion depth of the piston into the syringe housing. The piston stop can be formed both in the syringe housing and also on the piston itself. In the first case, the piston stop can be formed as a bulge, for example, a curvature directed inwards on the inner wall of the channel or a corresponding projection, which can be formed around the entire circumference or only along part of the circumference of the channel. In this first case, the piston stop serves as a constriction of the cross-section of the channel so that the rubber plug of the piston can not be pushed past the stop and thus a maximum insertion depth of the plunger into the syringe housing can be established. In the opposite case, wherein the piston stop is formed on the piston itself, said stop can be configured, for example, as a bulge or a projection on the piston rod which shapes (e.g., enlarges) the diameter of the piston in such a way that it can not be pushed further into the syringe housing.

In further embodiments of the device according to the invention, the continuous channel, i.e. the channel formed by the first channel and the second channel, can have a substantially constant diameter. In this case, small-scale diameter constrictions, such as the piston stop formed on the inner wall of the continuous channel, should be ignored. For example, the diameter at the first open end of the syringe body can correspond to the diameter at the second open end of the syringe body so that the continuous channel corresponds to the interior of a continuous hollow cylinder. In this case, it can be advantageous if the second open end of the syringe body attachment (lower end of the syringe housing), which, so to speak, represents the exit and the inlet, respectively, is arranged as a wide opening, and there is no tapering or diameter variation of the continuous channel between said opening and the first open end of the syringe body (upper end of the syringe housing). With a syringe housing configured in this way, a continuous liquid flow low in turbulence can be achieved during operation of the device.

In a further aspect, the invention relates to a pipette device which can optimally exploit the advantages of the syringe housing according to the invention. The pipette device according to the invention can have a first holding device, which is configured to receive a syringe housing according to the invention and hold it in a substantially vertical position, and a second holding device which is configured to hold a piston inserted into the syringe housing and to move it axially therein, wherein the first holding device and the second holding device are moveable relative to the pipette device. Axial movement of the piston within the syringe housing is understood to mean movement of the piston within the syringe housing along an axis which describes the longitudinal expansion of the syringe housing.

The purpose of the first holding device can be seen in holding and moving the syringe housing. The position of the extraction column (i.e., a syringe housing filled with a matrix material), in particular the second open end of the syringe body attachment, can be set by means of the first holding device. This allows, for example, to bring the second end of the extraction column which is configured to receive and deliver a liquid, to a sample surface. The flexible height adjustment of the extraction column enables the use of different samples or different types of samples with different container sizes.

The purpose of the second holding device can be seen in holding a piston inserted in the extraction column and to axially displace said piston inside the extraction column depending on whether an aqueous phase is to be transferred into or out of the extraction column. The piston can, for example, at its one end, for example, the front end, have a plug whose cross-section corresponds to the cross-section of the continuous channel of the extraction column, and at its other end, for example, the back end, have a holding part which, in manual operation of the syringe, corresponds to the thumb part. The plug, which may, for example, comprise rubber, can be mechanically coupled to the holding part by means of a piston rod. The piston can be introduced with the holding part, for example, into an insert provided in the second holding device and secured in this manner at or in the second holding device.

In order to vertically displace a syringe housing together with the piston, i.e., to change the distance between the outlet of the syringe housing and a sample located below said housing, without transferring a liquid into or out of the syringe, it is possible for the first holding device and the second holding device to be moved synchronously, that is to say without a relative movement between the first holding device and the second holding device. If, on the other hand, a liquid is to be transferred into or out of the extraction column, a relative movement between the first holding device and the second holding device is necessary. In order to provide this functionality, a first motor can be provided, which is configured, if necessary, to bring about a relative movement between the housing of the pipette device and the first holding device. Furthermore, a second electric motor can be provided, which is configured, if necessary, to bring about a relative movement between the first holding device and the second holding device. The pipette device may have a first pair of rails along which the first holding device can be displaced relative to the pipette device in one dimension, for example, vertically, (first relative movement) by means of the first motor. The pipette device may have a second pair of rails along which the second holding device can be displaced relative to the first holding device in one dimension, for example, vertically (second relative movement) by means of the second motor. Instead of rails, other can guiding means such as threaded rods can be used. The axis of the first relative movement can be parallel to the axis of the second relative movement.

In further embodiments of the pipette device according to the invention, said pipette device can have a first sensor which is configured to determine the distance between the first holding device and the second holding device. The first sensor can be configured, for example, as an acoustic, optoelectronic or as a mechanical distance sensor, in the latter case, for example, as a pressure-sensitive distance sensor with push button. However, for example, the sensor can also be implemented by means of a step counter and thus be integrated in the first motor or be a part thereof.

In further embodiments of the pipette device according to the invention, said pipette device can have a second sensor which is configured to determine the distance between a reference point of the pipette device and the first holding device or the second holding device. The statements made with respect to the first sensor apply analogously to the second sensor. From this distance, the position of the second holding device or correspondingly of the first holding device relative to the reference point can then also be determined via the relative position of the first holding device relative to the second holding device. The reference point can be any fixed point on the housing of the pipette device.

In further embodiments of the pipette device according to the invention, the first holding device can be configured as a movable base for the second holding device. In other words, the pipette device can be designed in such a way that, in the case of an active movement (i.e., intentional and directed movement, e.g., by means of an electric motor) of the first holding device, the second holding device is moved passively, since its bearing is arranged on the first holding device.

In further embodiments of the pipette device according to the invention, said pipette device can have a rotary plate which is arranged below the first holding device and is configured to receive samples, the rotary plate being capable of being rotated by means of a motor. The samples can be sample containers with various liquids or aqueous media, which, for example, are needed for purification by column chromatography (e.g., washing buffer for calibrating the matrix material, the sample containing the cells to be purified, washing buffer for removing non-specifically bound components of the sample, elution buffer for detaching the desired cells from the matrix material, etc.). By targeted selection of the number of samples and their contents, different process sequences can be carried out in which the interior of the syringe or a cleaning column, in particular the matrix material, together with affinity reagents, such as antibodies, adhered thereto, can be exposed to various aqueous solutions. In a process sequence, samples of different sizes can be used since the height at which the syringe is held can be adjusted simultaneously with each changeover to the next sample which is then positioned below the syringe. Executing such column chromatography purification protocols is known to the person skilled in the art.

In further embodiments, the rotary plate of the pipette device can be replaced with a means which moves samples arranged thereon along an axis or along two axes, thus enabling sample selection. In this case, the samples can be arranged one after the other in one or more rows, for example, on a rectangular area, such as a correspondingly configured sample holder. The selection of a sample can take place by moving the sample holder along axis or along two axes (simultaneously or successively) to position the desired sample below the syringe. Such a means lends itself for this purpose, for example, when several syringes are to be used in parallel next to one another in a purification. In this context, it is noted that the pipette device can be modified in accordance with various embodiments in such a way that the first holding device and the second holding device are configured to hold two or more pipette devices and to use them simultaneously.

EXAMPLES AND FIGURES

In the following, the device according to the invention is described by way of exemplary embodiments. The embodiments are only illustrative of the device according to the invention and should not be construed as limiting the scope in any way.

DESCRIPTION OF SPECIFIC EMBODIMENTS OF THE INVENTION

Figure 1:
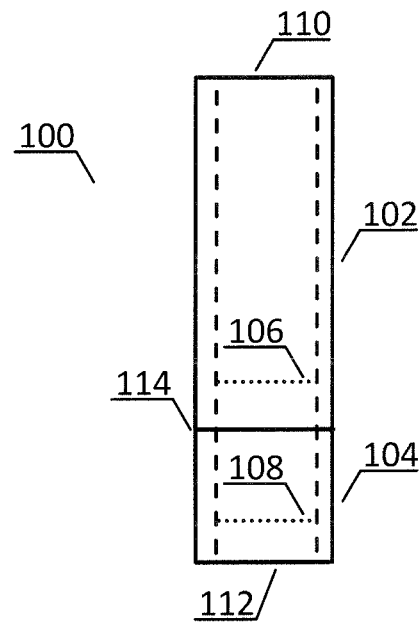
FIG. 1 shows a schematic structure of an exemplary syringe housing in a side view.

FIG. 1 illustrates a schematic structure of an embodiment of the invention of syringe housing 100. Here, the syringe housing 100 is illustrated in a side view. The exemplary syringe housing 100 has a syringe body 102 which has a first open end 110 and a second open end, with a first channel being formed between the two ends. The syringe body 102 has a first membrane 106, which extends over the cross-section of the first channel. The exemplary syringe housing 100 also has a syringe body attachment 104 which has a first open end and a second open end 112, a second channel being formed between these two ends. A second membrane 108 extends over the cross-section of the second channel. Both membranes 106, 108 are arranged substantially perpendicular to the longitudinal direction of the first and second channels. The second open end 112 of the syringe body 110 and the first open end 110 of the syringe body attachment 104 are designed so as to be connectable in a form-fitting manner and thus form the syringe housing 100. The second open end 112 of the syringe body attachment represents the outlet of the syringe housing 100, through which aqueous media/samples can be introduced into the syringe housing 100 and vice versa.

As can be seen from FIG. 1, the syringe body 102 and the syringe body attachment 104 in the assembled state form the syringe housing 100. FIG. 1 depicts a joint 114 which is indicating the boundary between the outer wall of the syringe body 102 and the outer wall of the syringe body attachment 104. The boundary between the inner wall of the syringe body 102 and that of the syringe body attachment 104 can be at a different level, which is explained in the following with reference to the further figures. At this boundary in the interior of the syringe housing 100 the second open end of the syringe body 102 and the first open end of the syringe body attachment 104 are in contact with one another and are therefore not shown in the schematic representation of the outer surface of the syringe housing 100. The two dashed, vertically extending lines indicate the channel passing vertically through the syringe housing 100, which is located in the interior of the syringe housing 100. The continuous channel is formed by merging the first channel (part of the continuous channel in the syringe body 102) and the second channel (part of the continuous channel in the syringe body attachment 104). The inner wall of the continuous channel, together with the two membranes 106, 108 bound part of the continuous channel, into which a desired matrix material can be introduced. As explained above, this part of the continuous channel can be functionally referred to as extraction volume, as in the extraction volume, a target substance can be extracted (filtered out) from aqueous phases by means of the matrix material. For example, the matrix material can be applied to the second membrane 108 in the open extraction volume before the two parts of the exemplary syringe housing 100 are connected, and the corresponding other part of the syringe housing 100 can then be connected with the first part, for example, screwed. Alternatively, the matrix material can also be applied to the first membrane 106 if the syringe body 102 is rotated by 180° (upside down) during filling. After the single connecting, the two parts forming the syringe housing 100 are non-detachably connected so that the syringe housing 100 can not be repeatedly opened and then reassembled. For this purpose, the mechanical interface between the two parts can be configured as a one-time fastening so that the syringe body 102 can not be detached again from the syringe body attachment 104. FIG. 1 shows the basic concept of the syringe body 100 according to the invention. It can be subject to numerous modifications and alterations, some of which are illustrated and discussed in the further figures.

Figure 2:
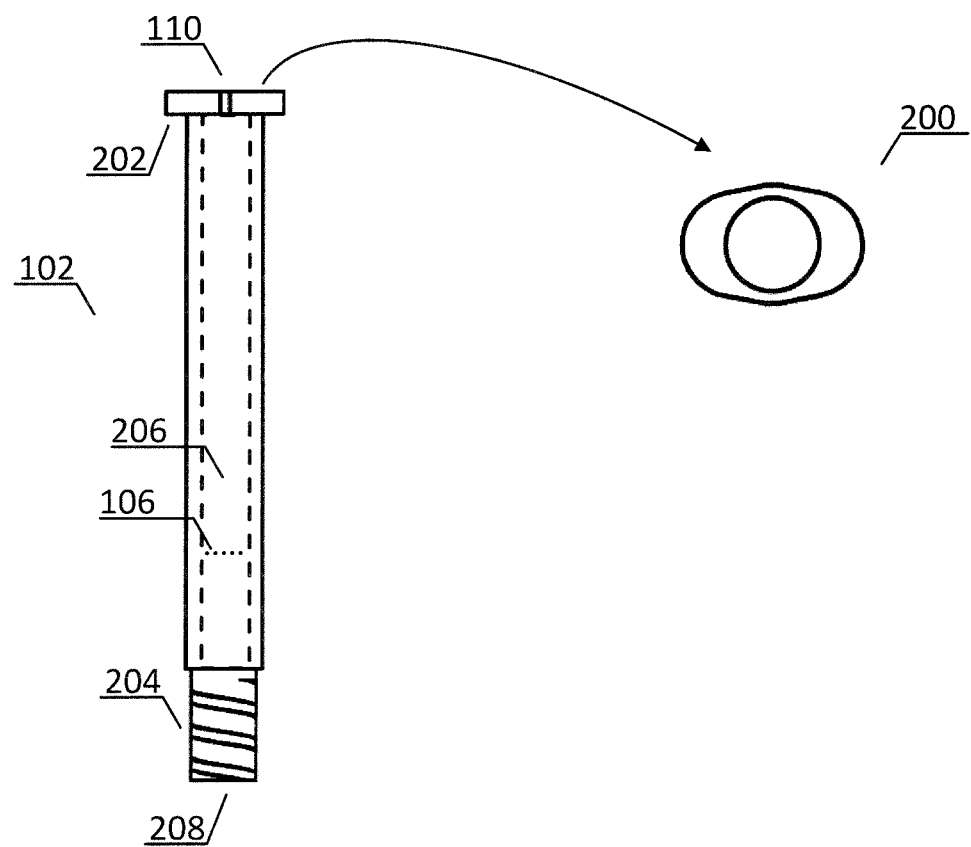
FIG. 2 shows an exemplary syringe body in a side and top view.

FIG. 2 illustrates, as a large image, a side view of an embodiment of the syringe body 102. The exemplary syringe body 102 can be designed as a hollow cylinder with a certain wall thickness. The inner wall of the hollow cylinder can define the first channel 206. The first channel 206 located on the inside of the syringe body 102 between the first open end 110 and the second open end 208 is indicated in the upper region by means of the dashed lines. In the lower region, the exemplary syringe body 102 has a smaller outer diameter and its outer wall is provided with a thread 204 in this embodiment. The thread is arranged as male thread on the outer surface of a collar which extends axially outwardly (downwards in FIG. 2) from the non-threaded portion of the syringe body 102. By means of the male thread 204, the syringe body 102 can be joined form-fittingly with a corresponding female thread of the syringe body attachment 104. The allocation of female and male threads to the respective components is arbitrary here, so that the female thread can also be arranged on the collar of the syringe body 102 and can be screwed into a male thread of the syringe body attachment 104. A finger flange 202 can be arranged at the first open end 110. A plan view 200 of the exemplary syringe body 104 is indicated on the right-hand side of the sheet by the curved arrow. Accordingly, the finger flange 202 can have an oval shape and be arranged around the first open end 110 of the syringe body. The shape of the finger flange 202 can be adapted to the use of the syringe housing 100, for example, to the use in a pipette device described further below, and, for example, may be also circular or rectangular.

The first membrane 106 is in the first channel 206, i.e. attached to or formed integrally with the inner wall of the syringe body 102, so that it does not cause any change in the diameter of the first channel 206, except for its membrane thickness. The first membrane 106 can be secured in the inner wall of the syringe body 102, for example, extending into said wall. The edge of the first membrane 106, for example, can be introduced into the syringe body 102 during the formation of said syringe body 102 and can thus be connected with its inner wall in a firmly bonded manner during this process. As a result, the first membrane 106 can be present in the first channel 206 without an additional holding ring onto which it is glued and pushed into the desired position within the first channel 206, or other fastening structures. Thus, there is no risk that, e.g., particles from the sample will adhere to such a fastening structure— for example, between the inner surface of the first channel 206 and the outer surface of a holding ring. Further, the first channel 206 can provide favorable flow characteristics since it has no flow-altering structures, such as edges or projections in its interior, which originate from possible fastening structures. Due to the position of the first membrane 106 within the first channel 106 that is to say by its distance from the second open end 112, the size of the extraction volume may be established. As a modification of the arrangement illustrated in FIG. 2, the first membrane 106 can also be arranged higher or lower within the vertically extending first channel 206, and it can also be arranged within the part of the syringe body 102, which is threaded by the thread 204.

Figure 3:
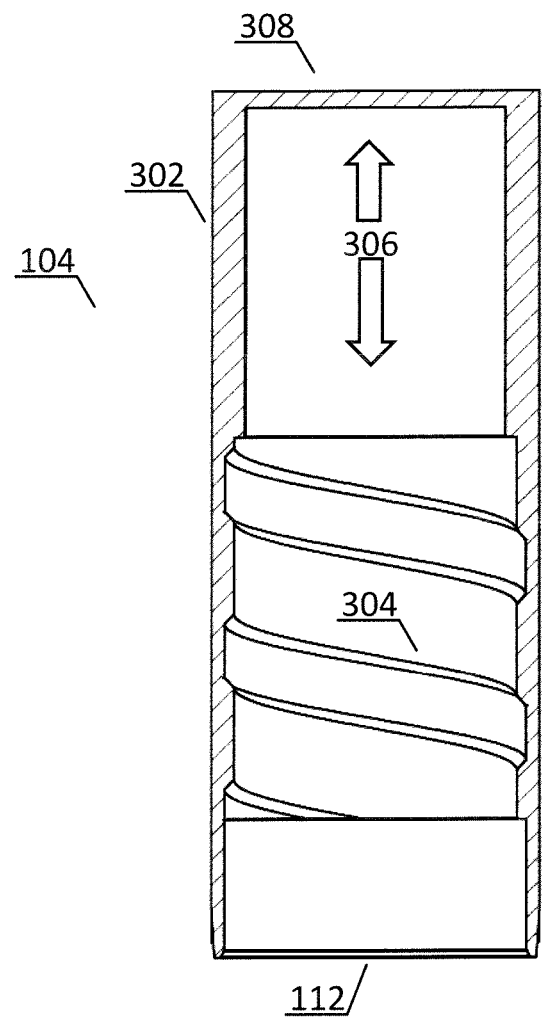
FIG. 3 shows an exemplary syringe body attachment in a side view.

FIG. 3 illustrates an exemplary syringe body attachment 104 which is suitable for the syringe body 102 of FIG. 2, also in a side view. The syringe body attachment 104 can be structured similar to the syringe body 102 in that it can also be configured as a hollow cylinder, in which a second channel 306 extends between its first open end 308 and its second open end 112, which can have a uniformly constant diameter, which can also correspond to the diameter of the first channel 206. Thus, the transition between the two subchannels 206, 306, which form the continuous channel of the syringe housing 100, can be without constrictions and continuous so that fluid flow between the two subchannels 206, 306 can occur without turbulence. When the syringe body 102 carries a male thread, then the thread 304 of the syringe body attachment is configured as a female thread (as shown in FIG. 3) and provided in the inner surface of the wall 302 of the syringe body attachment 104. The thread 304, which for a better illustration in FIG. 3 is shown as a structure arranged only in a subsection of the syringe body attachment 104, can start directly at the first open end 308 and thus enable joining with the syringe body 102 with minimal physical effort. The second membrane 108 has not been shown explicitly, it can be arranged at any location or any height within the second channel 306. For example, the second membrane 108 can be arranged at any location or any height below the thread 306 in the second channel 306 or in other words at any location or at any height of the second channel 306 in its non-threaded portion. The second membrane 108 can also be integrally connected with the wall 302 of the syringe body 104 in the same way as the first membrane 106 with the wall of the syringe body 102. Optionally, the first membrane 106 and/or the second membrane 108 may be adhesively bonded or otherwise secured to the corresponding open end with which the syringe body 102 or the syringe body attachment 104 is screwed, in such a way that it receives additional support from the edges of the syringe body 102 and the syringe body 104 pushing thereon. Although the edge of the second open end 112 of the syringe attachment 104 is shown as being flat, this is not an imperative characteristic. Depending on fluid-mechanical requirements, the edge of the second open end 112 can be implemented unevenly, for example, by having free spaces or recesses, which in turn define projections or webs, so that the lower end of the syringe housing does not rest on its entire circumference on a support.

Figure 4:
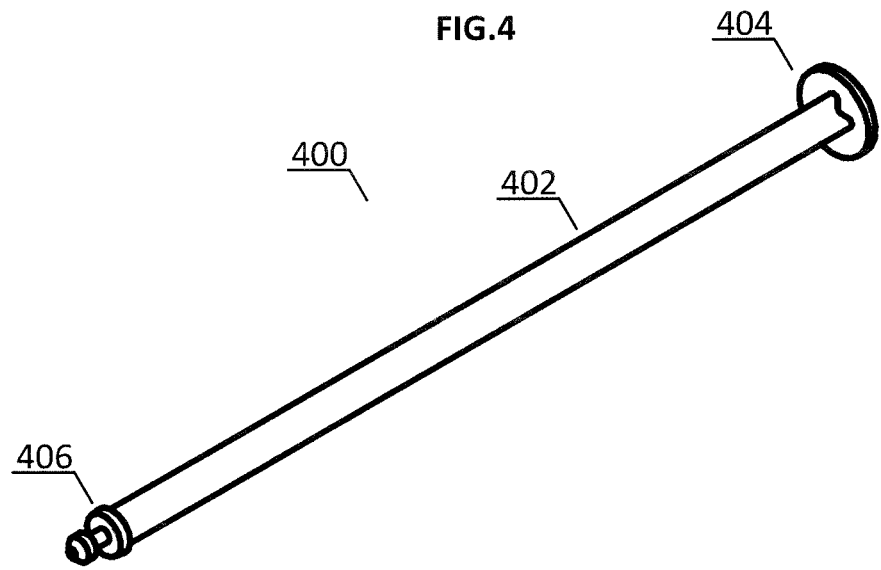
FIG. 4 shows an exemplary piston in a 3D view.

FIG. 4 shows an embodiment of a piston 400 which can be used in conjunction with the syringe housing 100 according to various embodiments to form a full-featured syringe. The piston 400 has a piston rod 402 which has a thumb part 404 at its back end and a piston head 406 at its opposite end, the front end. A corresponding rubber plug can be placed on the piston head 406, the entire circumference of which is fully in contact with the wall of the continuous channel and separates the two parts of the channel it separates in an air-tight manner. The rubber plug can be replaced by an unused or a disinfected rubber plug following an executed process sequence (for example, after a cell cleansing), whereby contamination of the contents of the syringe housing 100 with foreign substances can be prevented. Since the piston rod 402 together with the thumb part 404 does not come into contact with the contents of the syringe housing 100, these can be used without prior cleaning/disinfection. The thumb part 404 can be manually or mechanically pressed into or pulled out of the syringe housing 100. Depending on the length of the syringe housing 100 and the piston rod 402 adapted thereto, a stabilizing element can be arranged thereon between the piston head 406 and the thumb part 404. The stabilizing element can be, for example, at least one disc with a certain thickness, the edge of which is in contact with the inner wall of the continuous channel. However, the diameter of the disk can also be slightly smaller than the diameter of the continuous channel within the syringe body 100. The stabilizing element, however, can also be fins, which, for example, are each arranged on the piston rod 402 rotated by 90° relative to one another and extend as far as the inner wall of the syringe housing 100. By means of the stabilizing element, the piston rod 402 can be guided and centered within the syringe body 100. With a syringe housing 100 which is excessively long in relation to its cross-section, the correspondingly long piston rod 402 can thereby be guided securely in the interior of the syringe housing 100.

As already mentioned above, the piston 400 can have a piston stop which can serve to adjust its insertion depth into the syringe housing 100. The piston stop can be configured, for example, as a disc or a small plate which is arranged at a predetermined location on the piston rod 400 and extends in a plane perpendicular to the piston rod 400. The piston stop can increase the cross-section of the piston 400, in particular of the piston rod 402, in such a way that it can not be pushed further into the syringe housing 100 beyond the location at which the piston stop is attached. For example, the piston rod 400 can have a several locations at which such a piston stop can be mounted variably. In this way, a piston 400 can be very easily adapted to the desired insertion depth into the associated syringe housing 100 by displacing the piston stop to a different position on the piston 400 and thus can be used flexibly. As an alternative, the piston rod 402 itself can also be formed thicker from a certain location, so that its cross-section is greater than the cross-section of the opening at the first open end of the syringe body 102. In further embodiments of the piston 400, the thumb part 404 can also function as a piston stop because it has a cross-section which at least partially extends beyond the cross-section of the channel so that the thumb part 404 is also suitable for preventing an insertion of the piston 400 into the syringe body 100. The allowed insertion depth of the piston 400 into the syringe housing 100 can be predetermined by the position of the first membrane 106 which, when the piston 400 is pressed down, is obviously not to be perforated/destroyed by the piston plug placed thereon.

Figure 5:
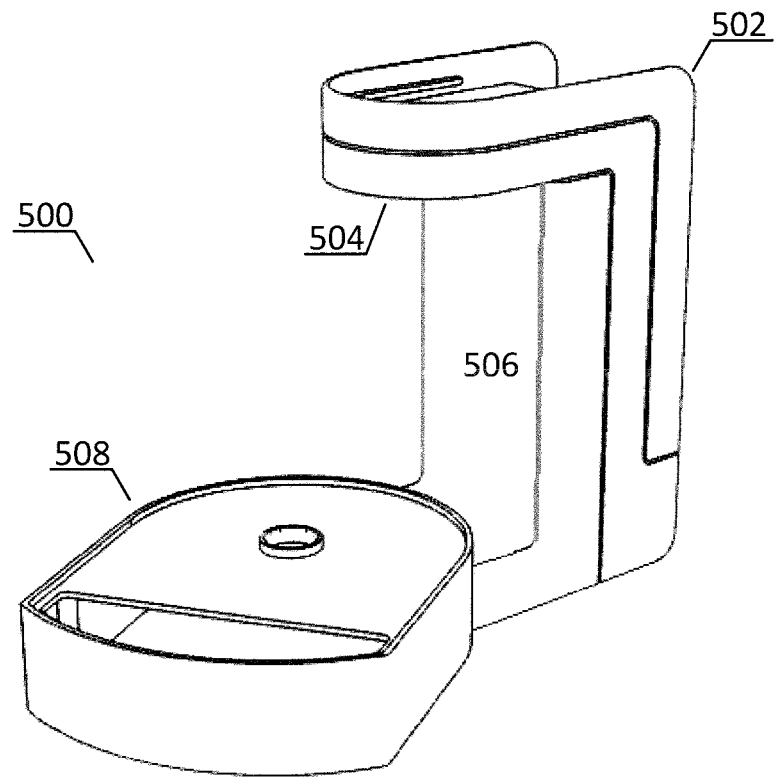
FIG. 5 shows a 3D side view of an exemplary pipette device.

FIG. 5 illustrates a perspective 3D view of an embodiment of a pipette device 500, in which the syringe housing 100 according to the invention together with the piston 400 can be used. The exemplary pipette device 500 may have a first holding device 504 and a second holding device 502. The first holding device 504 is configured to receive a syringe housing 100 according to the invention and to hold it in a substantially vertical position. The second holding device 502 is configured to hold and move axially a piston 400 inserted in the syringe housing 100. FIG. 5 shows that in the exemplary pipette device 500, the second holding device 502 is formed in an L-shaped manner and rests on the first holding device 504. The first holding device 504 serves, so to speak, as a movable base for the second holding device 502. The second holding device 502 can be moved relative to the first holding device 504, for example, by means of an electric motor. In this embodiment, the first holding device 504 likewise has a substantially L-shaped shape and, in turn, rests on a housing part 506. The first holding device 504 can be moved relative the housing part 506, for example, by means of an electric motor. A holder 508 on which a sample plate (not shown in FIG. 5) can be placed, is arranged on the housing part 506. The housing part 506 can be integrally connected to the holder 508 and together therewith form a stable housing base for the pipette device 500. The above-mentioned substantially vertical position of the syringe housing 100, for example, can correspond to a position in which the syringe body attachment 104 is directed downwards, that is towards the sample plate 508. This aspect is illustrated in particular in FIGS. 7A and 7B.

In the exemplary pipette device 500 shown in FIG. 5, said pipette device is shown in a retracted state in which an inserted syringe housing 100 would be held at the lowest possible point and a piston 400 inserted therein would be pushed as far as possible into the syringe housing 100. From the initial position illustrated in FIG. 5, the first holding device 504 can be moved vertically upwards relative to the housing part 506. The second holding device 502, in turn, can be moved vertically upwards relative to the first holding device 504. Both between the housing part 506 and the first holding device 504 and between the first holding device 504 and the second holding device 502, at least one rail or another functionally equivalent element can be arranged on which the components can be displaced relative to one another. In order to stress the electric motors as little as possible, it may be advantageous if the first electric motor, which moves the first holding device 504 up and down relative to the housing part 506, is arranged substantially in the housing part 506, and the second electric motor, which moves the second holding device 502 relative the first holding device 504 up and down, is substantially arranged in the first holding device. However, this arrangement of the electric motors is not absolutely necessary and deviating thereof has no effect on the exemplary pipette device 500 shown in FIG. 5.

Irrespective of the arrangement of the electric motors and the specific external appearance of the pipette device 500, the first holding device 504 and the second holding device 502 are movable relative to one another. In the embodiment of the pipette device 500 in FIG. 5 this may take place either by actively moving the second holding device 502 relative to the first holding device 504 (hereinafter, first movement mode) or actively moving the first holding device 504 relative to the housing part 506, and at the same time actively moving the second holding device 502 relative to the first holding device 504 in the opposite direction (hereinafter, second movement mode), so that only the first holding device 504 moves when looking from the outside and the second device 502 appears to be stationary (if both are moved at the same speed). The second movement mode is due to the design of the exemplary pipette device 500 shown in FIG. 5, in which the first holding device 504 functions as a movable base for the second holding device 502. The second movement mode can be considered less important for laboratory operation considering the functional assignment of the two holding devices 504, 502. Supporting the second holding device 502 on the movable first holding device 504 can be advantageous because, with the operation of only one electric motor, the entire syringe can be displaced upwards or downwards without the piston 400 inserted therein being moved. A movement of the piston 400 within the syringe body 100 is always associated with either a displacement of fluid from or an introduction of fluid into the syringe body 100. Therefore, the arrangement of the two holding devices 504, 502 in FIG. 5 is quite advantageous, since the case, where the syringe is displaced upwards or downwards and at the same time the fluid volume has to be adapted in the syringe, can be regarded as rather infrequent.

The embodiment of the pipette device 500 shown in FIG. 5 can be modified, for example, in such a way that the second holding device 502 is not supported by the first holding device 504 but is arranged diametrically opposite or diametrically displaced relative to the first holding device 504 so that instead of the first holding device 504 the housing part 506 functions as a base or support, relative to which the second holding device 502 can be moved independently of the first holding device 504. In such a structure, the first holding device 504 and the second holding device 506 can be moved independently of one another relative to the housing part 506 and consequently relative to one another. In the embodiment of the pipette device 500 shown in FIG. 5, this is not the case, as explained above, since an active movement of the first holding device 504 will result in a passive moving along of the second holding device 502. In addition, it should be emphasized that ultimately the specific form of the individual components of the pipette device 500 according to the invention is not limited to its representation in FIG. 5 but can be adapted clearly to design requirements, while retaining the core idea of the invention presented here.

Figure 6:
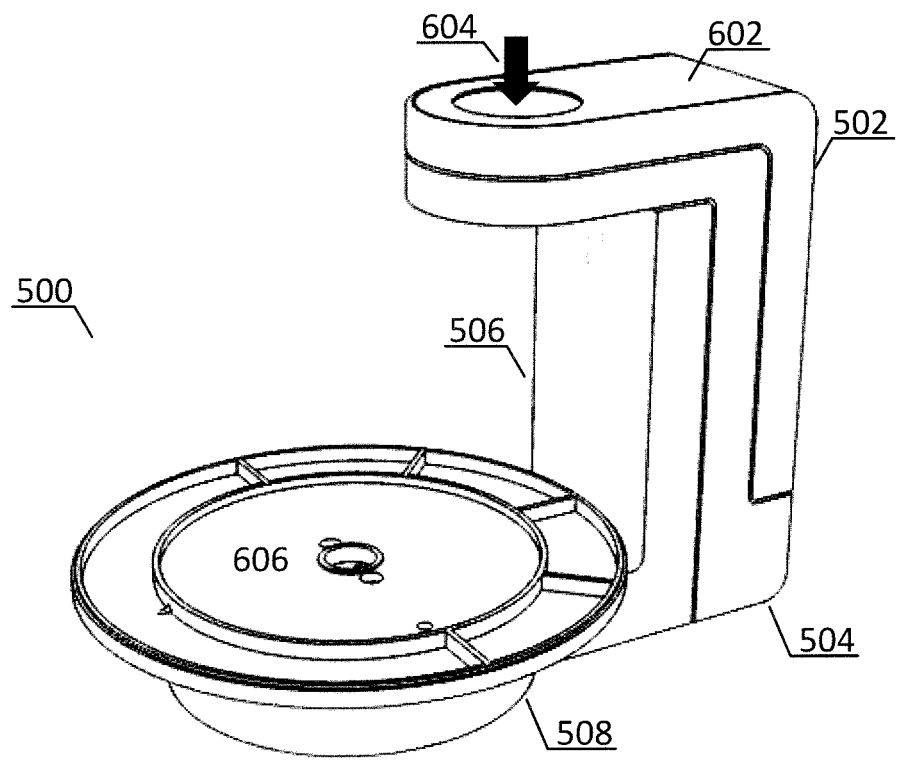
FIG. 6 shows a further 3D side view of an exemplary pipette device.

FIG. 6 shows a pipette device 500 which has a structure essentially identical to the pipette device shown in FIG. 5, in a perspective 3D view. Corresponding components are therefore provided with the same reference symbols and are not described again in detail.

FIG. 5 shows the second holding device 502 without the associated cover 602, which can be seen in FIG. 6. In the embodiment shown, the cover 602 is L-shaped and can be pushed onto the second holding device 502 from behind after a syringe housing 100 with piston 400 has been inserted into the pipette device 500. The arrow 604 is intended to indicate the position at which an inserted syringe is held under the cover 602 by the first holding device 504. For this purpose, an opening is provided both in the first holding device 504 and in the second holding device 502, the openings being arranged one above the other. In the manner in which the syringe housing 100 according to the invention together with piston 400 is inserted into the exemplary pipette device 500 and is held therein, is addressed in more detail in the description of FIGS. 7A and 7B. FIG. 6 also illustrates a sample plate 606 on which samples can be placed and can be brought into a position below the first holding device 504 and the second holding device 502 for processing. In other words, the sample plate 606 can be rotated as required to move various samples to a position below the first holding device 504 and the second holding device 502 in which a syringe (not shown in FIG. 5) inserted into the pipette device 500 according to various exemplary embodiments is held. The syringe can then be lowered into the corresponding sample and contacted with an aqueous phase present in the sample. This aspect is explained in more detail below with reference to FIGS. 7A and 7B.

Based on the exemplary pipette device 500, which is illustrated in a perspective 3D plan view in FIGS. 7A and 7B, in particular the starting up of the pipette device, which includes the insertion of the inventive syringe housing 100 according to various embodiments including piston 400, is explained below. Since the structure of the pipette device 500 shown in FIGS. 7A and 7B largely corresponds to the structure shown in FIGS. 5 and 6, corresponding components are therefore provided with the same reference symbols and are not described again in detail.

A feature which is not shown in FIGS. 5 and 6 is the digital control panel 702, which can have touch-sensitive control panels, with which the pipette device 500 can be operated, as well as additionally status indicators. The digital control panel 702 may be integrally formed with the housing part 506. With such a control panel 702, for example, process sequences (e.g. pipetting operations) can be started, interrupted, stopped or adjusted. The process sequences can be input, for example, from a data storage device via a data interface on the pipette device 500, for example, from a USB stick or an SD card. A process sequence can be understood to mean a predefined sequence of process steps, in which aqueous phases are transferred from the syringe housing 100 into a corresponding samples or from these into the syringe housing 100 in a predetermined time or at a predetermined rate. The insert into which the data storage device can be inserted can, for example, can be arranged on the housing part 506, such as below the sample plate 606 or in the vertically upwardly projecting part of the housing part 506. By retrieving predefined process sequence files from a miniaturized data storage device, the pipette device 500 according to the invention can be used very flexibly and can be used, for example, as a mobile unit outside the laboratory, since no computer (PC) is required for its operation. The pipette device 500 can have a battery in the housing part 506 for use as a mobile unit (or also independently thereof). Of course, the pipette device 500 according to the invention can also be coupled to a computer via a data interface and can be directly controlled therefrom. This data interface can be the same interface as for the connection of the data storage device, or a separate wireless interface (e.g. WLAN, Bluetooth or NFC).

Figure 7A:
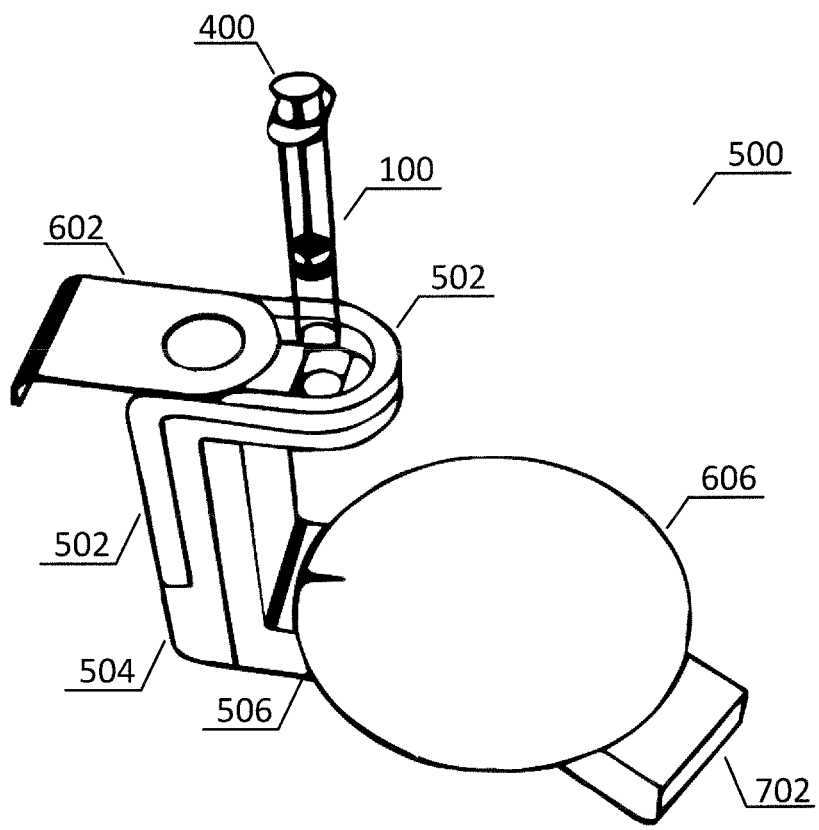
FIGS. 7A and 7B show 3D plan views of an exemplary pipette device before and after insertion of the syringe housing according to the invention together with the piston inserted therein.

FIG. 7A illustrates the pipette device 500 before inserting a syringe, in particular a syringe, comprising the syringe housing 100 according to the invention together with piston 400. For this purpose, the cover 602 can be pushed back and the syringe can be inserted into the opening provided in the first holding device 504 and in the second holding device 502. The opening in the first holding device 504 is designed in such a way that, on the one hand, the cylindrical part of the syringe housing 100 fits through the opening and extends downward from the first holding device 504 hanging freely, and on the other hand its finger wheel (see element 202 in FIG. 2) does not fit through the opening, but is locked in it. Viewed from the top, the cross-section of the projection of the opening can correspond to the cross-section of the syringe housing 100 so that the syringe housing 100 can be inserted into the opening up to the finger flange. After the syringe is inserted into the opening in the first holding device 504, the syringe is fixed laterally. In the edge of the opening furrows may be provided at least partially. The syringe can then be rotated in the opening by a certain angle so that the finger flange slides into the furrows and becomes additionally fixed by said furrows. In this way, the syringe can also be fixed vertically so that it no longer has any degrees of freedom relative to the first holding device 503. The furrows can be designed in such a way that the finger flange engages in the opening after the syringe has been rotated. As a result, the risk of a release of the syringe housing 100 by itself from the first holding device 504 during a process sequence can be eliminated. However, other securing mechanisms can also be provided which fix the syringe housing 100 to the first holding device 504, for example, brackets or holding clips.

The opening in the second holding device 502 is arranged above the opening of the first holding device. Its cross-section can be larger than the cross-section of the opening in the first holding device 504. The cross section of the opening in the second device 502 is in any case shaped in such a way that the syringe (including the finger flange) can be inserted through it into the opening in the first holding device 504. Thus, the shape of the opening in the first holding device 504 may be encompassed by the shape of the opening in the second holding device 502. After the syringe or the syringe housing 100 according to various embodiments has been inserted, the piston 400 can be inserted into the syringe housing 100 if it is not yet arranged therein. Subsequently, the piston 400 can be secured to the second holding device 502. This state is shown in FIG. 7B. For this purpose, a fixing element can be provided on the underside of the cover 602 which is configured to receive the thumb part (see element 404 in FIG. 4) of the piston 400. The fixing element in the exemplary pipette device 500 in FIG. 6 can be arranged approximately in the region marked with the arrow 604 (on the underside of the cover 602). The fixing element can be, for example, a semicircular or U-shaped element which has a groove on its inner side into which the finger flange 202 can be inserted from the open side of the fixing element. The inner side is understood to mean here the side which is facing the center of curvature of the fixing element. In this case, the fixing element arranged on the underside of the cover 602 is open towards the direction into which the cover 602 is also pushed onto or into the second holding device 502, that is, to the right side of the sheet in FIGS. 7A and 7B.

Figure 7B:
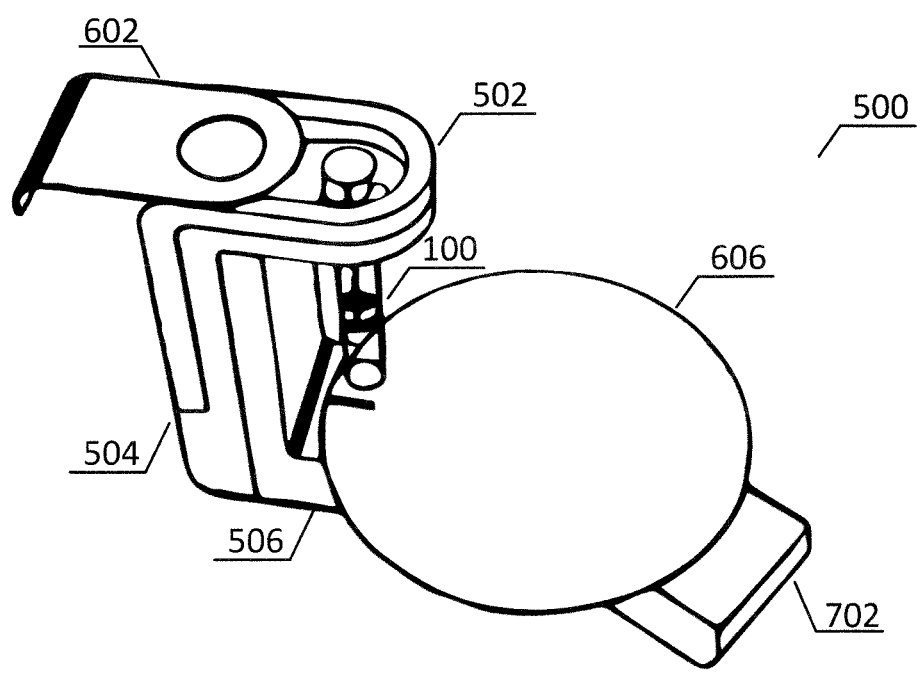

If the cover 602 is closed by pushing to the right onto the second holding device 502, from the starting point shown in FIG. 7B, the fixing element pushes with its open side forward over the finger flange 202 of the piston 400 and thereby fixes said finger flange entirely vertically and in cooperation with the fixed syringe housing 100, in which the piston 400 is present, also laterally around the entire circumference. The width of the opening in the groove of the fixing element can be adapted to the thickness of the finger flange 202 in such a way that the groove of the fixing element encompasses at least the edge of the finger flange 202 in a pincer-like manner. In other words, by sliding the cover 602 onto the finger flange of the syringe housing 100, the fixing element is inserted laterally at least partially in the finger flange 202. In order to facilitate the insertion of the finger flange 202 into the insert formed by the fixing element so that the finger flange 202 does not have to be brought up to the level of the groove of the fixing element before the cover 602 is pushed on, the groove can constantly increase in width from the open end of the fixing element and form a kind of collection funnel for the finger flange 202 so that said finger flange can be inserted into the fixing element from any position within a predetermined tolerance range (which is determined by the width of the groove at the open end of the fixing element).

Figure 8:
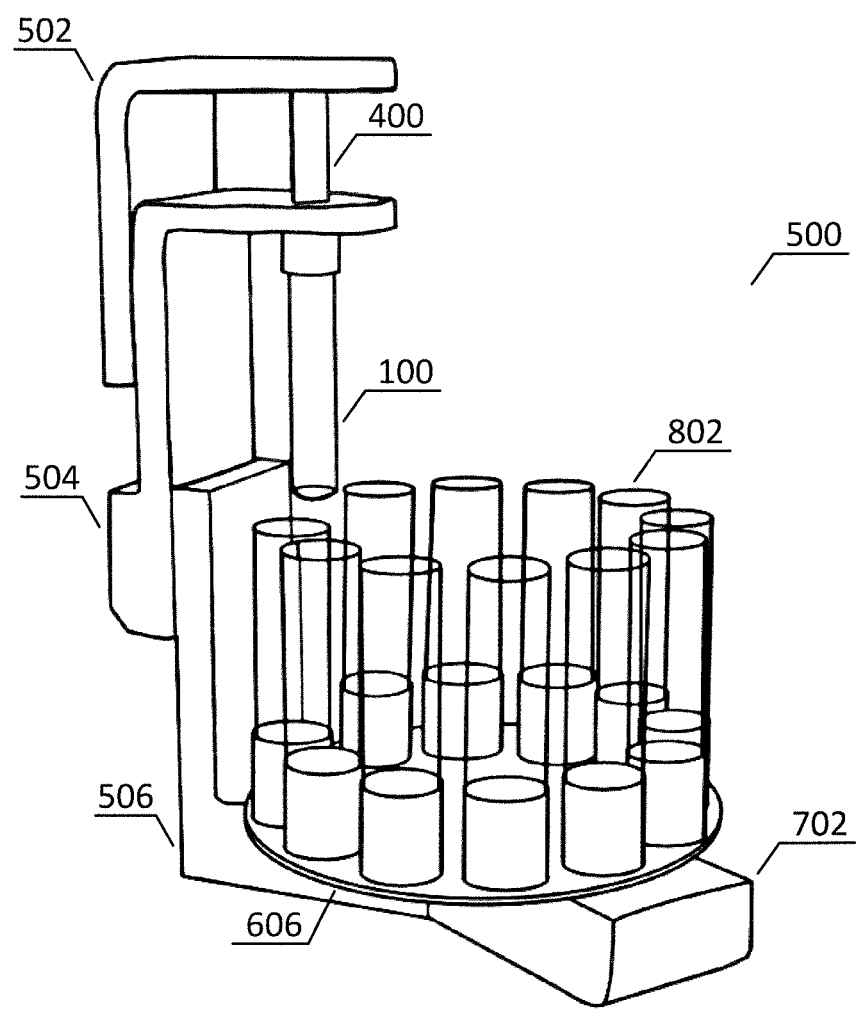
FIG. 8 shows a 3D side view of an exemplary pipette device with the syringe according to the invention inserted.

After the cover 602 has now been pushed onto the second holding element 502 and the finger flange 202 of the piston 400 has engaged the fixing element, the pipette device 500 is prepared for operation. FIG. 8 shows a snapshot of the exemplary pipette device 500 during operation. The samples 802 arranged on sample plate 606 can be placed below the syringe or the syringe housing 100 in a predetermined sequence. When a desired sample 802 has been moved below the syringe, said syringe can be lowered into the sample 802 below and the aqueous solution therein can be transferred into the syringe or an aqueous solution can be transferred from the syringe into the corresponding sample 802. As shown in FIG. 8, the first holding device 504 is responsible for positioning the syringe body 100 according to the invention, while the second holding device 502, to which the piston 400 is secured by means of the finger flange 400 (not visible in FIG. 8) is responsible for displacing the piston 400 within the syringe. Although all sample containers 802 illustrated in FIG. 8 are of the same size, of course, sample containers 802 of different sizes can be used in a process sequence as a benefit of the pipette device 500 according to the invention is the possibility of vertical adjustment of the syringe or of the syringe housing 100. The size of the samples 802 used in a process sequence can be defined in advance in a file (sequence file) belonging to this process sequence. Alternatively or additionally, the pipette device 500 according to the invention can have at least one filling level sensor, so that, on the one hand, the size of the currently selected sample vial 802 and also the filling level thereof can be determined automatically during the process sequence. The filling level sensor can be an optical or acoustic sensor. The distinction between the height of the currently selected sample container 802 and its filling level can be made on the basis of a change in the reflection which depends on whether the signal emitted by the filling level sensor hits an empty region of the sample container 802, a filled region of the sample container 802, or none of the two. The filling level sensor can be arranged, for example, in the section of the housing part 506, which is located in front of the sample vessel 802 which has just been selected. In addition, the filling level sensor can be vertically movable within the housing part 506, for example, by means of an electric motor, so that a kind of input operation can be carried out with each newly selected sample container 802 in order to determine its size and filling level.

In the present case a syringe has been described which has a two-part syringe housing in which a region separated by two membranes is provided (extraction volume), and a piston. By means of a special connection of the two syringe housing parts with one another, the syringe can be configured, for example, as a disposable syringe. The two parts of the syringe housing can be connected to one another via a one-way screw fastening with or without a gasket. The syringe body can be provided, for example, with a membrane on the lower threaded part. The syringe body attachment can have spacers at its lower end, which prevent resting of the lower end with its entire circumference on a flat surface. The syringe body can carry a bulge both in the lower part and in the upper part, which serve as piston stops. The piston stop can also be implemented by means of an adaptation of the piston rod.

The division of the syringe housing described in this application according to various embodiments by means of the two membranes, allows the introduction of buffer media into the extraction volume formed by the membranes. The buffer media allow, for example, proteins, cells or other biological materials to be separated.

The syringe housing introduced here can be used to form a disposable syringe which is designed in such a way that, by means of a special fastening, for example, a rotary or plug-in fastening or a mixed form thereof, reusing the syringe is prevented and any uncertainties in the laboratory with regard to the content of such a disposable syringe can be eliminated.

The syringe housing described here is characterized by the fact that by means of the form-fitting anchoring of the membranes in the syringe housing, for example, by introducing said membranes into the syringe housing during the injection molding process, continuous transitions can be created between the compartments and thus biological components remaining at steps between the compartments can be greatly minimized or even completely prevented. At the same time, the maximum size of the particles to be passed through can be determined by the selection of the membrane to be introduced, for example, by the choice of its pore size.

Using the syringe housing described here, the separating medium present in the extraction volume can be separated from the end product. Thus, in one working step, an isolation of cells, for example, can be carried out. The syringe housing can be used fully automated in the described pipette device.

Figure 9:
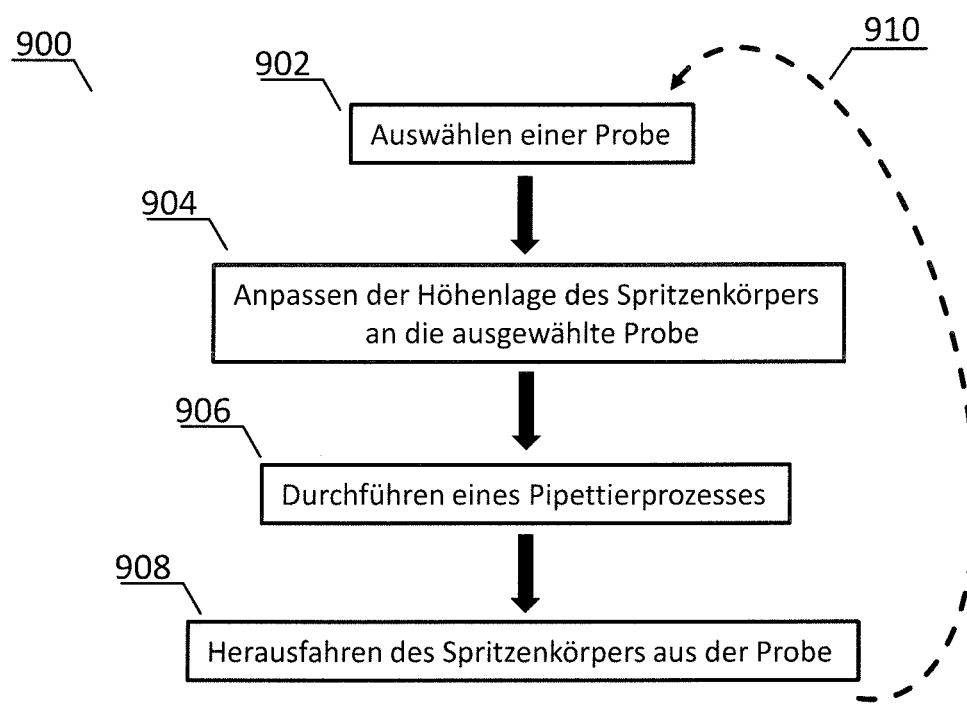
FIG. 9 shows a flow diagram illustrating an exemplary subsequence within a pipetting operation (purification step) of a biological material which can be carried out by means of the pipette device according to the invention.

FIG. 9 shows a flow diagram 900, which illustrates an exemplary subsequence within a pipetting operation of a biological material. The subsequence can be understood as a type of basic operation which can be carried out several times on various samples 802 during the execution of a pipetting operation by means of the pipette device according to various embodiments.

The basic sequence illustrated in FIG. 9 can start with a step 902, in which a sample is selected. The sample to be selected can be a sample 802 which is arranged on the sample plate 606 of the pipette device 500 according to various embodiments. For this purpose, the sample plate 606 can be rotated so that the sample 802 to be selected is positioned below the syringe or below the sample syringe housing 100. The samples 802 can be arranged on the sample plate 606 in such a way that the syringe housing 100 can be introduced into each sample 802, which is brought below the syringe housing 100 according to the invention by rotating the sample plate 606. In other words, the syringe housing 100 and the selected sample can be arranged concentrically with respect to one another when viewed in cross-section from above or from below, the cross-section of the corresponding sample vessel 802 being usually larger than the cross-section of the syringe housing 100. In order to ensure correct positioning of the samples 802, the sample plate 606 can have a positioning mask, which can be attached to the sample plate 606 and which has openings into which the samples 802 can be inserted. Such a positioning mask may have openings of different sizes to accommodate samples 802 of different sizes and process them in one pipetting operation. In principle, the sample positions can be predefined on a rotary plate or a corresponding means, i.e., it can be predefined at which sample location which sample content (e.g. Blood, buffer solution, biotin, etc.) may be found. The start position of the sample plate can be determined automatically by the pipette device, so that, for example, a purification program sequence always starts at the start position of the sample plate. In principle, a purification operation can be carried out by means of the pipette device according to various embodiments by selecting a predetermined program which is suitable for this purpose on the pipette device. In the pipette device 500 according to various embodiments, the starting position can correspond to a specific location of the sample plate 508. For this purpose, for example, in the sample plate 508 a gap (indentation) can be arranged in the middle between two sample insertion locations. The gap can be encoded as a position 0 (zero) and used to define a starting position (zero position). The starting position can be detected by means of a sensor, for example, a Hall sensor. After inserting a sample plate 508 into the pipette device 500, said pipette device can be configured in such a way that the sample plate 508 is moved into the starting position. Subsequently, a purification operation can be carried out starting from the starting position, wherein the movement of the sample plate 508 can be precisely determined in the associated purification program sequence (e.g. the sequence of different successively selected sample insert positions) and the currently selected position can be monitored, for example, by means of a step counter starting from the starting position.

After a sample 802 has been selected in step 902, in a subsequent step 904, the height position of the syringe body 100 can be adapted to the selected sample 802. Prior to each selection of a sample 802 in step 902, first the syringe held by the first holding device 504 and the second holding device 502 can be moved into an initial position which ensures that no sample 802 arranged on the sample plate 606 collides with the syringe housing 100. This step may be required when samples 802 of different sizes (e.g., of different diameters) are used, which can usually also cause a different sample height. The initial position can be, for example, a position in which the first holding device 504 has moved a maximum distance upwards, that is to say by a position of the first holding device 504 with a maximum upward stroke. If, however, the heights of the sample containers 802 on the sample plate 606 are known, the initial position may correspond to a position in which the sample 802 with the greatest height can be moved below the syringe housing 100 without collision therewith. After selecting a sample 802, the syringe housing 100 can be lowered again so that, for example, the lower edge of the syringe housing 100 is in contact with a medium present in the selected sample 802. The lowering of the syringe can be carried out by moving the first holding device 504 and the second holding device 502 synchronously downwards. The synchronous movement ensures that no relative movement takes place between the syringe housing 100 and the piston 400, as a result of which either the medium would be displaced from the syringe housing 100 or air would be drawn into the syringe housing 100.

After lowering the syringe housing 100 into the selected sample 802 which has been moved below the syringe housing 100, a relative movement can take place between the first holding device 504 and the second holding device 502 if necessary, wherein, for this purpose, only the second holding device 502 is moved which induces movement of the piston within the syringe housing 100 according to the invention. This operation may initiate the next step 906, in which a pipetting process takes place. Depending on whether the second holding device 502 is moved up or down, an aqueous medium from the selected sample 802 can be transferred into the syringe housing 100 or from the syringe housing 100 into the sample 802. Of course, this process can be carried out several times, depending on the nature of the method to be carried out, for example, when the extraction yield is to be increased by passing a medium multiple times through the extraction volume.

After the pipetting process has been completed, the syringe body 100 can finally be removed from the selected sample 802 in step 908 so that subsequently another sample 802 arranged on the sample plate 606 can be selected and can be moved below the syringe housing 100. In this case, the syringe body 100 can be moved back into the initial position, so that, when the sample plate 802 is rotated, neither of the samples 802 can collide with the syringe housing.

The dashed arrow 910 indicates that step 902 with respect to another selected sample 802 can follow moving the syringe body 100 from the selected sample. By combining different samples 802 with different pipetting processes, complex pipetting operations can be carried out fully automated on the biological material.

In the present description, the structure of the pipette device has been explained with reference to embodiments, the functional description being based on the syringe housing with the two membranes. However, the pipette device can also be used with a syringe which is based on the syringe housing according to the invention but does not have the two membranes. In other words, the syringe housing presented in this description can be used in the pipette device according to various embodiments, for example, as extraction column housing. However, the function of the pipette device as such would not be impaired if syringes which do not have the two membranes are used. In other words, although the two membranes provided in the syringe housing according to the invention may be advantageous or even essential for the purpose of forming an extraction column, they are not relevant for the functionality of the pipette device. Rather, the pipette device can be used with any syringes which have a suitable shape and can be operated with a piston.

The invention claimed is:

1. A syringe housing for pipetting a biological material, comprising:
   a syringe body which has a first open end and a second open end, a first channel being formed between the two ends;
   a first membrane which is arranged such that the membrane extends substantially perpendicularly to the longitudinal direction of the first channel over the cross-section thereof;

a syringe body attachment which has a first open end and a second open end, a second channel being formed between the two ends;

a second membrane which is arranged such that the membrane extends substantially perpendicularly to the longitudinal direction of the second channel over the cross-section thereof;

wherein the second open end of the syringe body and the first open end of the syringe body attachment are designed so as to be connectable in a formfitting manner and thus form the syringe housing, the first channel and the second channel form a continuous channel in the connected state of the syringe housing, and the first membrane and the second membrane define an extraction volume in the region of the continuous channel.

2. The syringe housing according to claim 1, wherein the first membrane is integrally formed with the inner wall of the syringe body.

3. The syringe housing according to claim 1, wherein the diameter of the first channel in the region above the first membrane substantially corresponds to the diameter of the first channel in the region below the first membrane.

4. The syringe housing according to claim 1, wherein the transition from a region above the first membrane to a region below the first membrane is continuous.

5. The syringe housing according to claim 1, wherein the first membrane is secured to the end of the first channel.

6. The syringe housing according to claim 1, wherein the second membrane is integrally formed with the inner wall of the syringe body attachment.

7. The syringe housing according to claim 1, wherein the diameter of the second channel in the region above the second membrane substantially corresponds to the diameter of the second channel in the region below the second membrane.

8. The syringe housing according to claim 1, wherein the transition from a region above the first membrane to a region below the first membrane is continuous.

9. The syringe housing according to claim 1, wherein the first membrane is secured to the second open end of the syringe body.

10. The syringe housing according to claim 1, wherein the extraction volume has a substantially uniformly constant diameter.

11. The syringe housing according to claim 1, wherein the second open end of the syringe body and the first open end of the syringe attachment are designed to form a one-way fastening.

12. The syringe housing according to claim 11, wherein the one-way fastening is a plug-in fastening or a rotary fastening.

13. The syringe housing according to claim 11, wherein the one-way fastening has locking structures configured to prevent detaching of the syringe body from the syringe body attachment in the assembled state of the syringe housing.

14. The syringe housing according to claim 1, wherein the second open end of the syringe body and the first open end of the syringe body attachment are designed such that one of the open ends has an axially protruding collar which in the assembled state of the syringe housing engages an inwardly stepped region of the corresponding other open end.

15. The syringe housing according to claim 1, further comprising:

a piston which is axially displaceably supported in the interior of the syringe housing; and preferably a piston stop configured to limit the insertion depth of the plunger in the syringe housing.

16. A pipette device comprising:

a first holding device configured to receive a syringe housing according to claim 1 and to hold it in a substantially vertical position;

a second holding device configured to hold and axially move a plunger inserted in said syringe housing;

wherein the first holding device and the second holding device are movable relative to the pipette device.

17. The pipette device according to claim 16, further comprising:

a first sensor configured to determine the distance between the first holding device and the second holding device.

18. The pipette device according to claim 16, further comprising:

a second sensor configured to determine the distance between a reference point of the pipette device and the first holding device.

19. The pipette device according to claim 16, wherein the first holding device is configured as a movable base for the second holding device.

20. The pipette device according to claim 16, further comprising:

a rotary plate which is arranged below the first holding device and configured to receive samples, the rotary plate being rotatable by means of a motor.

* * * * *